US00PP23003P2

(12) United States Plant Patent
Denardi et al.

(10) Patent No.: US PP23,003 P2
(45) Date of Patent: Sep. 4, 2012

(54) APPLE TREE NAMED 'MONALISA'

(50) Latin Name: ***Malus domestica* Borkh.**
Varietal Denomination: Monalisa

(75) Inventors: Frederico Denardi, Caçador (BR); Anisio Pedro Camilo, Caçador (BR)

(73) Assignee: EPAGRI, Santa Catarina (BR)

( * ) Notice: Subject to any disclaimer, the term of this patent is extended or adjusted under 35 U.S.C. 154(b) by 30 days.

(21) Appl. No.: 12/931,845

(22) Filed: Feb. 11, 2011

(51) Int. Cl.
*A01H 5/00* (2006.01)

(52) U.S. Cl. ..... Plt./161

(58) Field of Classification Search ..... Plt./161, Plt./156
See application file for complete search history.

*Primary Examiner* — Susan McCormick Ewoldt
(74) *Attorney, Agent, or Firm* — Michelle Bos

(57) ABSTRACT

A new apple tree (*Malus domestics* Borkh) 'Monalisa' is described. 'Monalisa' is a 'Gala'-type apple notable for its high resistance to scab and glomerella leaf spot, resistance to red spider mite, low chilling requirement and uniform red-purple skin color.

2 Drawing Sheets

Latin name: *Malus domestica* Borkh.
Variety denomination: 'Monalisa'.

BACKGROUND OF THE VARIETY

'Monalisa' is a new and distinct cultivar of apple tree *Malus domestica* Borkh. This new cultivar is the product of a controlled cross of female parent 'Gala' (U.S. Plant Pat. No. 3,637) and male parent 'Malus 4' (not patented), carried out at the Epagri/Caçador Experimental Station at Caçador, Santa Catarina, Brazil in 1988. 'Monalisa' is characterized by, and was initially selected for, its high resistance to scab (*V. inaequalis*), high resistance to glomerella leaf spot (*C. gloeosporioides*), resistance to red spider mite (*P. ulmi*), low chilling requirement and uniform red-purple skin color with russeting. The variety was first asexually reproduced in 2001 at the Caçador Experimental Station by grafting onto 'M-9' rootstock. 'Monalisa' has been observed to remain true to type over successive asexually propagated generations.

BRIEF DESCRIPTION OF THE VARIETY

'Monalisa' was first selected for its high resistance to scab (*V. inaequalis*), high resistance to glomerella leaf spot (*C. gloeosporioides*), resistance to red spider mite (*P. ulmi*), low chilling requirement and uniform red-purple skin color with russeting. 'Monalisa' is distinguished from 'Gala' and from similar variety 'Cripps Pink' (U.S. Plant Pat. No. 7,880) and other known varieties, by these characteristics, as well by its intense over-color and its high acidity.

BRIEF DESCRIPTION OF THE PHOTOGRAPHS

Figure 1:
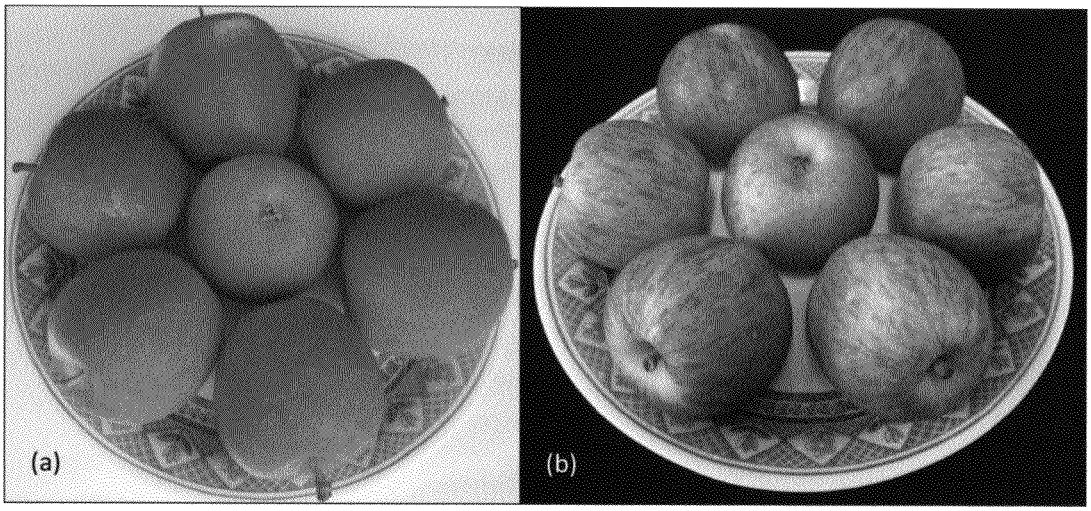
Figure 2:
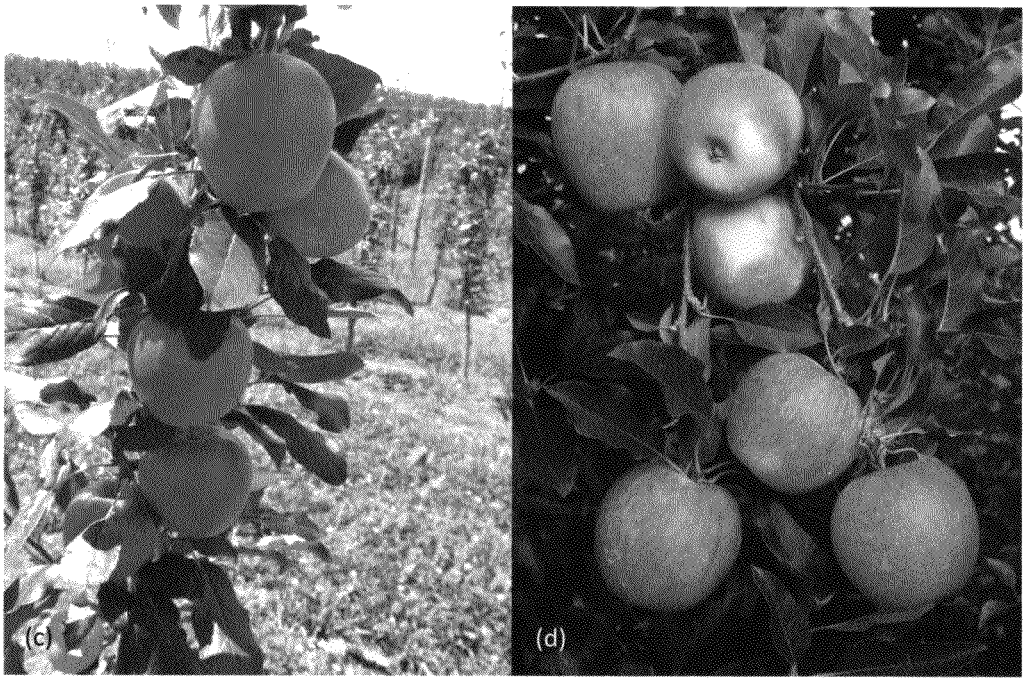

FIG. 1 shows fruit of 'Monalisa' (a) as compared to fruit of "Royal Gala" ('Tenroy' variety, U.S. Plant Pat. No. 4,121) (b); and FIG. 2 shows fruit of 'Monalisa' (c) as compared to fruit of 'Gala' (d).

DETAILED BOTANICAL DESCRIPTION OF THE VARIETY

The following-detailed botanical description is based primarily on observations made during the 2009 growing season Fraiburgo, Santa Catarina, Brazil of trees planted in 2001 ('M-7' rootstock) and 2007 ('Maruba'/'M-9' rootstock). All colors are described according to The Royal Horticultural Society Colour Chart. The characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor.*—Medium.
- *Type.*—Ramified.
- *Habit.*—Spreading.
- *Height.*—2.55 m on Maruba/M-9 rootstock at 3rd leaf.
- *Trunk diameter (at 30 cm above the graft).*—3.24 cm on Maruba/M-9 rootstock at 3rd leaf.
- *Bark coloration.*—Brown 200B.

Branch (fruiting branches located at around 1 m above the graft union):
- *Length.*—64.0 cm.
- *Diameter.*—11.4 mm.
- *Crotch angle.*—80° on average.
- *Bark color.*—Brown 200A.
- *Lenticel length.*—1.1 mm.
- *Lenticel color.*—Greyed-yellow 162A.
- *Number of lenticels per cm$^2$.*—8.5.

One year old shoot:
- *Length.*—20.4 cm.
- *Color.*—Brown 200A.
- *Pubescence.*—Weak to medium.
- *Thickness.*—Thin.
- *Internode length.*—27.5 mm.
- *Pubescence.*—Variable (weak at base and medium on top).
- *Number of lenticels per cm$^2$.*—8.5.

Flower buds:
- *Quantity per spur.*—1.2.
- *Shape.*—Ovate.
- *Length.*—9.8 mm.

*Diameter.*—5.2 mm.
*Color.*—Greyed-orange 165A.

Flowers:
*Diameter of fully open flower.*—42 mm.
*Relative position of petal margin.*—Free.
*Number per cluster.*—5 (average).
*Date of first bloom.*—September 15.
*Date of full bloom.*—September 25.
*Pollination requirement.*—Pollinator required; 'Golden Delicious' and 'Granny Smith' are good pollinators for 'Monalisa'.

Petals:
*Number per flower.*—5.
*Shape.*—Wide-ovate.
*Length.*—21 mm.
*Width.*—12 mm.
*Apex.*—Rounded.
*Base.*—Rounded.
*Margin.*—Smooth.
*Coloration of upper surface.*—White NN155D with spots of red-purple 68D.
*Coloration of lower surface.*—White NN155D with spots of red-purple 68D.
*Pistil size.*—8.2 mm.
*Pistil color.*—Green 142D.
*Stigma size.*—1.2 mm.
*Stigma color.*—Green white 157D.
*Style size.*—7.6 mm.
*Style color.*—Green 142D.
*Ovary size.*—2.5 mm.
*Ovary color.*—Yellow-green 149D.
*Anthers*—Quantity average 17.8 per flower.
*Anther size.*—Diameter 2.22 mm; Length 3.67 mm.
*Presence of pollen.*—Present.
*Color of pollen.*—Yellow 2D.
*Pedicel length.*—27.1 mm.
*Pedicel diameter.*—2.4 mm.
*Color.*—Green 140C.
*Sepals.*—Quantity 5 (average).
*Sepal color.*—Green 140D.
*Sepal shape.*—Acuminate.
*Sepal margin.*—Smooth and pubescent.

Leaves:
*Shape.*—Ovate.
*Length.*—12.0 cm.
*Width.*—7.2 cm.
*Length/width ratio.*—1.7 (long and narrow).
*Blade margin.*—Serrate.
*Apex.*—Acuminate.
*Base shape.*—Irregular.
*Color of upper surface.*—Green 131A.
*Color of lower surface.*—Green 138A.
*Attitude in relation to shoot.*—Outward.
*Petiole length.*—5.7 cm.
*Petiole diameter.*—1.8 mm.
*Petiole color.*—Green 138D with red-purple 71B at the base.

Fruit:
*Quantity per cluster.*—6 (average).
*Diameter.*—73.8 mm.
*Weight.*—170 g (varies with climatic conditions).
*General shape in profile.*—Conical.
*Position of maximum diameter.*—Below equator.
*Ribbing.*—Absent to weak.
*Crowning at calyx end.*—Absent to weak.
*Size of eye.*—4.2 mm.
*Aperture of eye.*—7.3 mm.
*Length of sepal.*—4.1 mm.
*Bloom of skin.*—Absent to weak.
*Greasiness of skin.*—Moderate (moderately strong after cold storage).
*Background color of skin.*—Yellow-white 158D.
*Amount of over color.*—80-100%.
*Over color of skin.*—Red-purple 59A.
*Intensity of over color.*—Medium to strong.
*Pattern of over color.*—Solid flush.
*Amount of russet around stalk cavity.*—Absent to very small.
*Amount of russet on cheeks.*—Absent to very small.
*Area of russet around eye basin.*—Absent to very small.
*Length of stalk.*—27.1 mm.
*Thickness of stalk.*—2.4 mm.
*Depth of stalk cavity.*—12.5 mm.
*Width of stalk cavity.*—32.5 mm.
*Depth of eye basin.*—12.7 mm.
*Width of eye basin.*—30.6 mm.
*Firmness of flesh.*—9.5 kg/cm$^2$ (21 lb/cm$^2$).
*Flesh texture.*—Fine.
*Aroma.*—Weak.
*Juiciness.*—Medium to strong.
*Brix.*—Medium to high (13.5% TSS).
*Flesh coloration.*—Yellow 4D.
*Stem coloration.*—Yellow-green 153B.

Seeds:
*Quantity per fruit.*—8.1.
*Shape.*—Long conical.
*Coloration.*—Green-purple N187A.

Harvest:
*Time for harvest.*—End of January (same time as 'Gala').
*Number of picks.*—Two.
*Amount of fruit produced per tree per harvest.*—85 fruits per tree (on dwarfing rootstock).

Disease & pests resistance/susceptibility: Scab Vf (*Venturia inaequalis*) resistance; Gala leaf spot (*Colletotrichum gloeosporioides*) resistance; Bitter rot (*Glomerella cingulata*) resistance; Mildew (*Podosphaera leucotricha*) tolerance; Red spider mite (*Panonychus ulmi*) resistance.

Market use: Fresh.

The invention claimed is:

1. I claim a new and distinct apple tree substantially as described and illustrated herein.

* * * * *